United States Patent [19]

Carroll, Jr.

[11] 4,203,034
[45] May 13, 1980

[54] DIFFRACTION CAMERA FOR IMAGING PENETRATING RADIATION

[75] Inventor: Edward E. Carroll, Jr., Gainesville, Fla.

[73] Assignee: University of Florida Board of Regents, Tallahasee, Fla.

[21] Appl. No.: 911,666

[22] Filed: Jun. 1, 1978

[51] Int. Cl.² .................. G01N 23/20; G21K 1/06
[52] U.S. Cl. .................................................. 250/280
[58] Field of Search ........................................ 250/280

[56] References Cited

U.S. PATENT DOCUMENTS

| | | |
|---|---|---|
| 2,688,094 | 8/1954 | Dumond . |
| 3,079,501 | 2/1963 | Birks, Jr. . |
| 3,160,749 | 12/1964 | Spielberg . |
| 3,628,040 | 12/1971 | Schnopper et al. .................. 250/280 |
| 3,898,455 | 8/1975 | Furnas, Jr. .......................... 250/280 |

Primary Examiner—Alfred E. Smith
Assistant Examiner—T. N. Grigsby
Attorney, Agent, or Firm—Harold L. Stowell

[57] ABSTRACT

A diffraction camera type imaging device for x-rays/gamma rays/neutrons employs at least one single crystal bent to conform to the radius of a sphere of radius 2R and ground to fit snugly on a Rowland sphere of radius R will, when rotated about an axis normal to the axis of symmetry of the crystal or translated rectilinearly along said axis of symmetry, focus, by Bragg diffraction, a two-dimensional x-ray/gamma ray/neutron radiating object to a two dimensional image.

6 Claims, 6 Drawing Figures

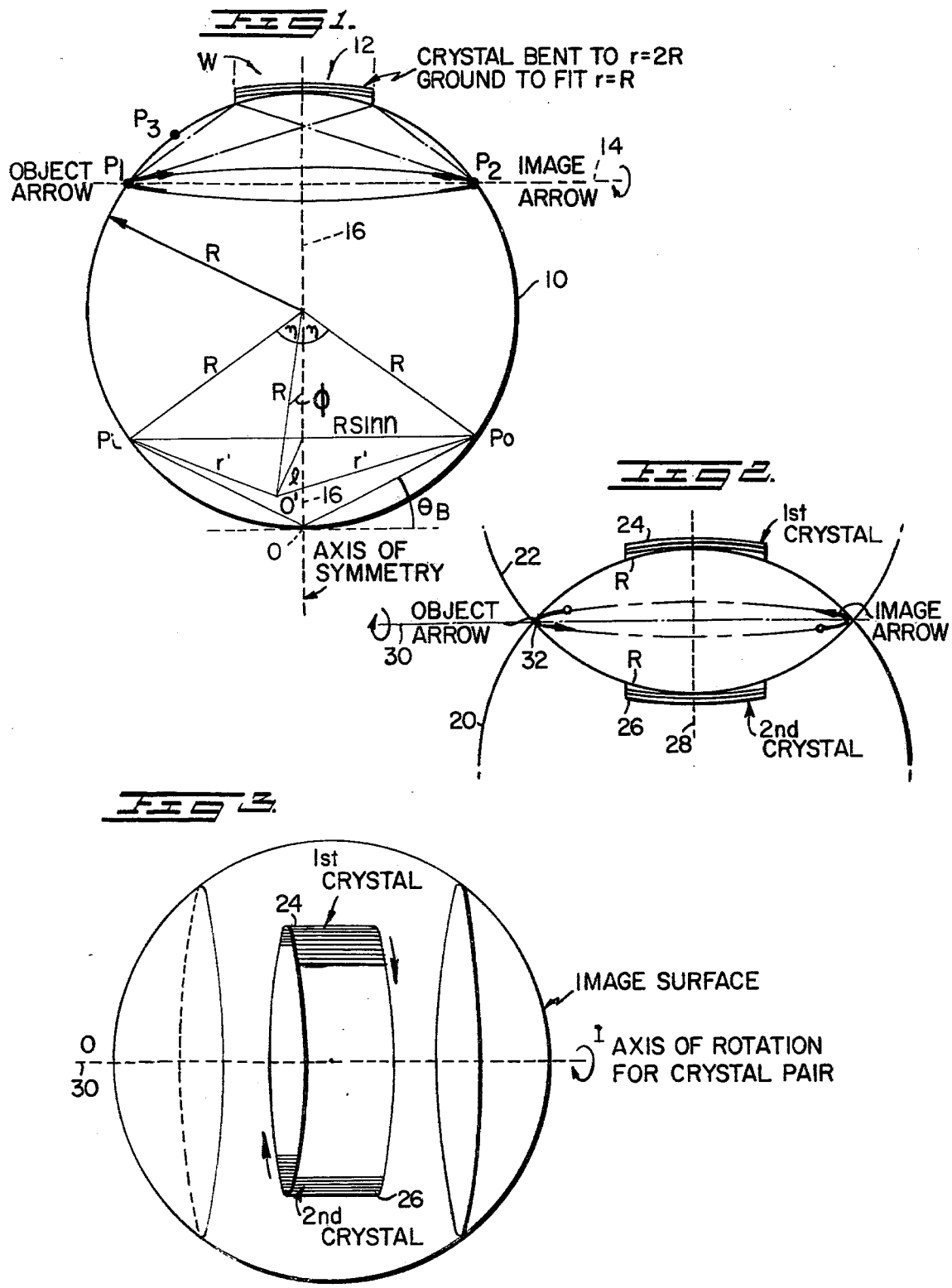

TRANSLATION CAMERA

3 CRYSTAL PAIRS ⇒ 3 IMAGE ARROWS
ROTATION SWEEPS OUT THE OBJECT/IMAGE SURFACES

DIFFRACTION CAMERA FOR IMAGING PENETRATING RADIATION

BACKGROUND OF THE INVENTION

1. Field of the Invention

This invention relates to a diffraction camera type two-dimensional imaging device for x-ray/gamma ray/neutron radiating object.

2. Description of the Prior Art

A major portion of the field of nuclear medicine involves the use of penetrating radiation (x-rays, gamma rays, or neutrons) to diagnose the presence of tumors in the body or to study organ function. Most often this involves the introduction into the body of tracer quantities of radioisotopes with subsequent imaging of the gamma or x-radiation emitted in their decay, e.g. introduction of radio-iodine has unique capabilities in studies of the function of the thyroid or the indication of the presence of nodules or other abnormalities. Other imaging techniques involve the irradiation of organis with penetrating radiation with subsequent imaging of nonradioactive elements present in the body, e.g. Americium-241 gamma rays have been used to stimulate production of characteristic iodine x-rays in the thyroid which are subsequently imaged for diagnostic purposes.

Certain constraints exist on such techniques which have substantially limited their capabilities:

(a) There are physiological limits on the quantities of radio-pharmaceuticals which may be used, hence the gamma or x-ray luminosity of the organ or function to be imaged is weak.

(b) Conventional optical systems (lenses) cannot be used since x-rays or gamma rays cannot be refracted practically. Hence more primitive optical systems have been used such as pin-hole cameras, mechanical collimators with scanning techniques, etc. These are characterized by low efficiency for imaging and limited resolution capability, or both. Some efforts have been made to develop imaging systems based on Fresnel zone-plate lenses or glancing incidence x-ray optics. These are invariably characterized by very low efficiency or a very small field-of-view.

Diffraction cameras and monochromators have also been used; however, most of the interest in curved crystal, diffraction optical systems has been in the fields of crystal structure studies, x-ray/gamma ray energy spectrometers, x-ray microscopy of surfaces, studies of molecular structure via observation of diffraction patterns, etc. Hence, most interest has resided in the production of a very fine point focus of monochromatic x-radiation. There has been little, if any, interest in using such optics to produce large images.

There is also known a (Berreman, DuMond, and Marmier, *Rev. Sci. Inst.* 25 1219 (1954) and D. W. Berreman, *Rev. Sci. Inst.* 26, No. 11, 1048 (1955) system which uses a doubly-bent single crystal of quartz to monochromatize and focus an x-ray beam to an extremely small point for x-ray diffraction studies. The 0.052 planes of quartz were used, the crystal was 3.8 cm$\times$7.6 cm$\times$0.025 cm thick, ingeniously bent to two different radii of curvature to produce a point image less than 0.5 mm in diameter at one meter from the crystal. The authors observed 2.78% reflection coefficient for Cu $K_\alpha$ radiation at $\theta_\beta=71°42'$. Using the 0.023 planes of quartz, Berreman calculated the reflection coefficient should be 1.6%. The devices they describe are based on the following physical concepts:

If a single flat crystal with atomic planes parallel to the large surface is bent to conform to the surface of a sphere of radius 2R and if it is ground to fit snugly on a sphere of radius R, then a luminous x-ray object point on the (Rowland) sphere at point $P_1$ will be exactly focused by Bragg diffraction to a point image at $P_2$, also on the sphere. All of the crystal will contribute to the image with a reflection coefficient $\rho$. This is frequently called the Johansson geometry.

SUMMARY OF THE INVENTION

I have found it possible to exploit the x-ray/gamma ray/neutron imaging capabilities of doubly bent single crystals to form a diffraction camera for nuclear medical imaging. The improved camera has a resolution of less than one millimeter and an efficiency at least as good as currently used mechanical collimators.

My invention may be generally defined as a diffraction camera type imaging device for x-rays/gamma rays/neutrons. It employs at least one single crystal bent to conform to the radius of a Rowland sphere of radius 2R and grount to fit snugly on a Rowland sphere of radius R. It will, when rotated about an axis normal to the axis of symmetry of the crystal or rectilinearly translated along the axis of symmetry, focus, by Bragg diffraction, a two dimensional x-ray/gamma ray/neutron radiated object as a two dimensional image.

It is an object of the present invention to provide a diffraction camera whereby nuclear medical imaging for diagnostic purposes will be greatly enhanced in that the imaging system has higher efficiency thus permitting lower doses and is capable of better resolution, fraction of a millimeter vs. one to a few millimeters. Where both objectives are achieved, the invention will result in lower patient doses with more precise information available to the physician. Earlier detection of abnormalities and more accurate diagnosis of organ function with lower absorbed doses would be the end product.

It is a further object to provide such an imaging system based on diffraction of x-rays/gamma rays from doubly bent single crystals, having good efficiency and much finer resolution than currently used mechanical collimators or pinhole cameras.

Another object is to provide such a device which is inherently tomographic, permitting lamino-graphic studies and which is based on well-established technology.

The invention will be more particularly described in reference to the accompanying drawings.

BRIEF DESCRIPTION OF THE DRAWINGS

FIG. 1 is a diagrammatic illustration of a simple form of the invention;

FIG. 2 is a view like that shown in FIG. 1 employing a pair of crystals;

FIG. 6 illustrates a form of the invention wherein three pairs of crystals are translated rectilinearly.

DESCRIPTION OF THE PREFERRED EMBODIMENTS

Figure 3:
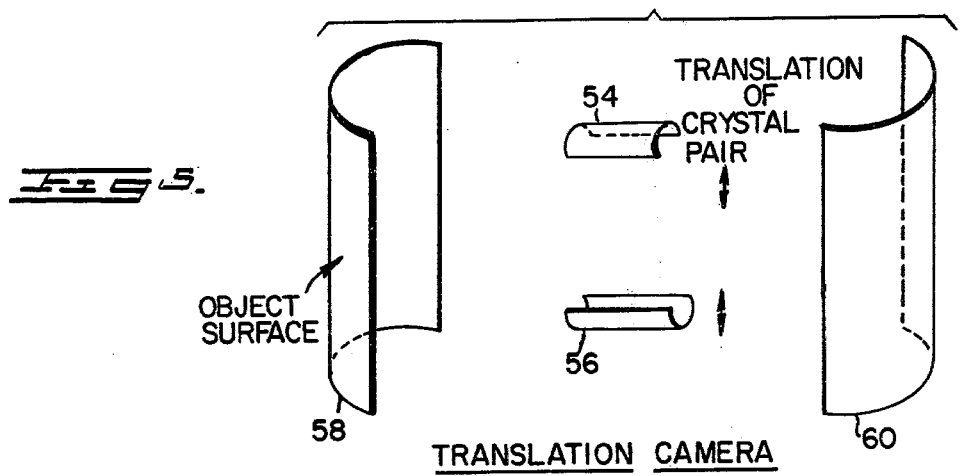
FIG. 3 shows how the crystals of FIG. 2 sweep out curved object and image surfaces by rotation about the indicated axis.

Referring to FIG. 1, diagrammatically illustrating the simplest form of the present invention, 10 generally designates a Rowland sphere of radius R; 12 designates a crystal such as quartz, Lithium Fluoride or, for example, pyrolytic graphite. The single flat crystal 12, with its atomic planes parallel to the large surface is bent to conform to the surface of a Rowland sphere of radius 2R and it is then ground to fit snugly on the Rowland sphere 10 of radius R. With this assembly, a luminous x-ray object designated P1 (and illustrated as an arrow positioned on the surface of the Rowland sphere 10) is exactly focused by Bragg diffraction to the surface indicated at P2 on the sphere, when the crystal 12 is rotated about axis 14 which is normal to the axis of symmetry 16 of the crystal. All of the crystal 12 will contribute to the image P2 with a reflection coefficient $\rho$. This is frequently referred to as the Johansson geometry. There is a limitation on how wide the crystal dimensions W may be which is dependent on the natural line width of the radiation employed with the camera.

Every ray from object P1 which strikes the crystal 12 is at the Bragg angle $\theta_B$ where $\lambda = 2d\sin\theta_B$ for first order scattering and d is the atomic interplanar spacing. An object at P3 will be imaged at a symmetric image across the sphere if its wavelength $\lambda'$ is shorter and if $\lambda' = 2d\sin_B'$.

There is a limitation on the useful widths (w) of crystals used as described in the camera which depends on the natural line width of the radiation used. If a ray from the center of the object s-rikes the center of the diffracting crystal 12 at a glancing angle $\theta_B$, it will strike the transverse edge of the crystal at a slightly different angle $\theta_B + \delta\theta_B$. If the natural line width of the radiation being observed is too small, there may be no photons with the correct $\lambda$ to equal $2d\sin(\theta_B + \delta\theta_B)$ and the edge of the crystal will not contribute to the intensity at the image. In FIG. 1:

0' = Center of crystal
0' = Transverse edge of crystal
$\theta_B = \pi/2 - \tan^{-1} R\sin\eta/[R(1-\cos\eta)]$
$\theta_B + \delta\theta_B = \pi/2 - \tan^{-1} R\sin\eta/l$
where $l = R[1 + \cos^2\eta - 2\cos\eta\cos\phi]^{1/2}$
Hence $$\delta\theta_B = \tan^{-1}\left(\frac{\sin\eta}{1 - \cos\eta}\right) - \tan^{-1}\left[\frac{\sin\eta}{[1 + \cos^2\eta + 2\cos\eta\cos\phi]^{\frac{1}{2}}}\right]$$

where $$\eta = \tan^{-1}\left[\frac{2\sin\theta_B \cos\theta_B}{1 - 2\sin^2\theta_B}\right]$$

if w/2 is the "effective" halfwidth of the crystal (useful halfwidth) then $$\phi \approx \frac{w}{2R}$$

For the iodine K x-ray width let us assume the reasonable value of 0.0004 Å, so we wish to reflect wavelengths from 0.4346 Å to 0.4354 Å, i.e., $\theta_B$ from 0.15320 radians to 0.15348 radians, i.e., $\delta\theta_B = 0.00028$ radians. Thus the maximum useable width of the crystal is w where $$.00028 = \tan^{-1}\left(\frac{\sin\eta}{1 - \cos\eta}\right) - \tan^{-1}\left[\frac{\sin\eta}{[1 - \cos^2\eta - 2\cos\eta\cos\phi]^{\frac{1}{2}}}\right]$$

where $$\eta = \tan^{-1}\frac{2(.1527).9883}{1 - 2(.1527)^2} = .3066 \text{ radians}$$

and $$\phi \approx \frac{w}{100}$$

$$.00028 = 1.41748 - \tan^{-1}\left[\frac{.30182}{[1.90891 - 2(.95337)\cos\frac{w}{100}]^{\frac{1}{2}}}\right]$$

therefore w=0.369 cm. Thus, the fraction of the (5 cm × 10 cm) crystal area which is useful for a particular object point is $0.369/5 = 0.074 = F_{Iodine\ K\ x-rays}$.

Employing a pair of spaced crystals in the imaging camera provides a system with twice the diffraction efficiency. Referring to FIGS. 2 and 3, 20 and 22 represent intersecting Rowland spheres and 24 and 26 represent first and second crystals mounted on a common axis of symmetry 28 with the curved surfaces having the radii R of each of the intersecting Rowland spheres in opposed relationship. Rotating the spaced crystals 24 and 26 about axis 30, normal to the axis of symmetry 28, of the pair of crystals will sweep out an image of the object 32 as depicted in FIGS. 2 and 3.

The crystals 24 and 26 are constructed as previously described in respect to crystal 12 of FIG. 1 in that the crystals are first bent to a radius 2R and then ground to fit the radius R of the Rowland spheres.

Figure 4:
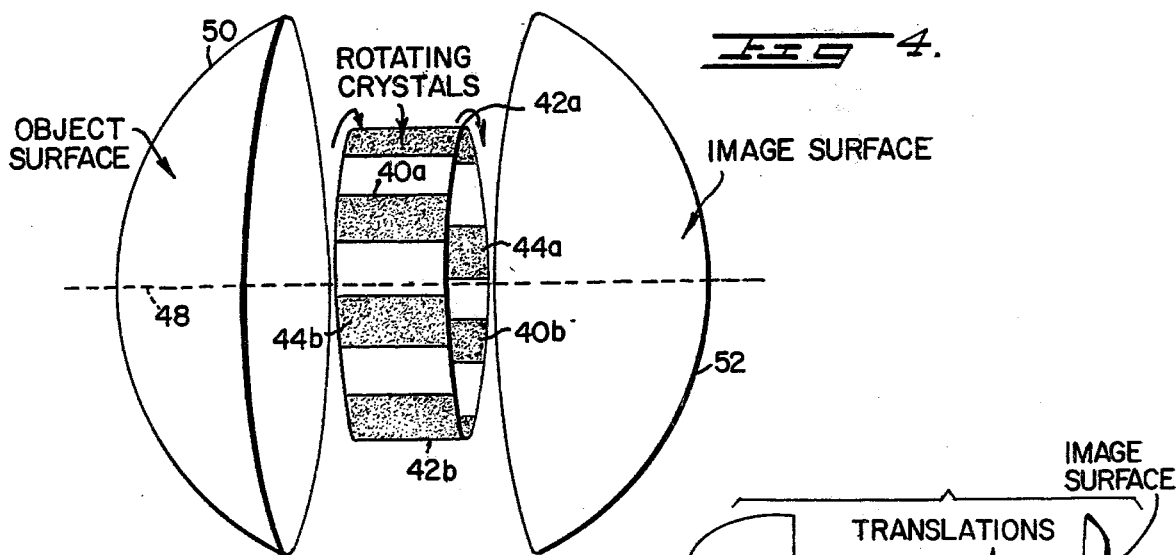
FIG. 4 illustrates a modified form wherein three pairs of crystals are employed and rotated.

Referring to FIG. 4, there is shown a camera like that shown in FIGS. 2 and 3 employing three pairs of rotating crystals designated 40a and 40b; 42a and 42b; and 44a and 44b. The crystals 40a . . . 44b are each constructed as disclosed in reference to FIG. 1 and are positioned on intersecting Rowland spheres. Adding the additional pairs of crystals around the axis of rotation 48 increases efficiency proportionately in sweeping out from the object surface 50 to an image surface 52.

Figure 5:
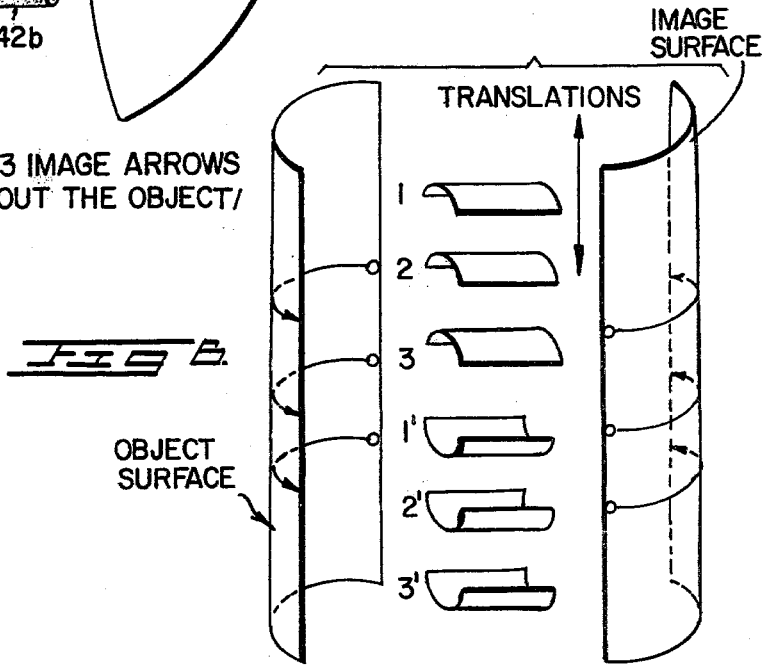
FIG. 5 illustrates a form of the invention wherein the pair of crystals are translated rectilinearly in respect to the object surface.

Rather than rotating the crystals the crystals may be translated rectilinearly along the axis of symmetry of the crystals. FIG. 5 depicts diagrammatically this form of the invention wherein 54 and 56 are doubly bent crystals bent to a radius 2R of the selected Rowland sphere and ground to fit the radius R of the Rowland sphere. Mounting said pair of crystals on spaced intersecting Rowlands spheres and moving the pair of crystals 54 and 56 as indicated by the directional arrows in FIG. 5 will sweep out a cylindrical object surface 58 to a cylindrical image surface 60. This form of the invention is particularly advantageous as the image surface 60 which may be a sheet of sensitive film is easy to form into and retain in a cylindrical configuration.

Referring now to FIG. 6, three pairs of crystals designated 1, 2, 3 and 1', 2', 3' are mounted for translation in the direction of the directional arrow to sweep out the cylindrical object surface into a cylindrical surface. The crystals 1, 2, 3, 1', 2', 3' are constructed and mounted in accordance with the discussion in respect to FIG. 5.

In respect to the rotation type camera, FIGS. 1–4, the camera has the following characteristics (all characters in reference to FIG. 1).

1. The crystal mounting ring has radius $2R\sin^2\theta_B$.
2. Object and image surfaces lie on the sphere of radius $2R\sin\theta_B\cos\theta_B$.
3. Image illumination is most intense at the center and drops off away from the center (as in pinhole cameras).
4. If object point O emits S gamma rays, then $S(\Omega\rho F)$ gamma rays pass through image point I where $\Omega$ is the solid angle subtended by each crystal at O and $\rho$ is the reflection coefficient of the crystal. F is the fraction of the area of the crystal which can reflect because of the limited line-width of the radiation used.
5. Resolution at I will depend on (a) mosaic spread of the crystal and (b) precision of bending, grinding and mounting. It is expected that (b) will be dominant and should rather easily be kept at <1 mm.

EXAMPLE I

Two large LiF crystals are cleaved along the 220 planes ($d = 1.424$ Å) and then plastically bent to the correct radius and then ground and etched and mounted. LiF is strongly reflecting with excellent stability, hard, with small imperfection and typically individual mosaic blocks are 500 Å in size and mis-oriented with respect to each other by 10 sec of arc or greater on the average. If carefully bent, a negligible increase in mosaic spread would result. ($\lesssim$ few seconds of arc for reasonable radii).

Imaging of Iodine Fluorescent X-rays

For thyroid scans the crystal ends position about 10 cm from the thyroid. Hence, radius of the focal sphere is 15 cm. $\lambda(28.5\text{keV})=0.435$ Å and So $\theta_B=8°47'$, $\sin\theta_B=0.1527$, $\cos\theta_B=0.9883$. This determines the Rowland sphere radius as $$R = 15/2\sin\theta_B\cos\theta_B = 49.7 \text{ cm.}$$

Thus, the crystals are bent to a radius of 99.4 cm, and ground to a radius of 49.7 cm. Distance between centers of faces of the crystals is the diameter of the crystal mounting circle $$D = 4R\sin^2\theta_B = 4.64 \text{ cm.}$$

Crystals are rigidly mounted as a pair with provisions for micrometer adjustments of the relative orientation and spacing to assure correct alignment and minimum resolution.

EXAMPLE II

A translation camera, rather than a resolution camera, is advantageous since the organ to be imaged may be irradiated with a thin beam of gamma rays, i.e., minimize the dose by irradiating only the portion of the object surface which may be imaged anyway. The efficiency of the translation camera device is considered to be as follows:

(a) assume a point object is emitting S x-rays per second. Then the efficiency of imaging is $$\epsilon = \frac{\text{No. of x-rays passing through image point}}{S} =$$

$$\begin{pmatrix}\text{Fractional solid}\\\text{angle subtended}\\\text{at the object}\\\text{by the crystals}\end{pmatrix}\begin{pmatrix}\text{Reflection}\\\text{coefficient}\\\text{of the crystals}\end{pmatrix}\begin{pmatrix}\text{Wavelength}\\\text{Factor}\end{pmatrix} = \Omega\rho F$$

The reflection coefficient will be estimated as 0.05, and F is obtained as 0.074 of the total crystal area to yield $$\epsilon = 2 \times 10^{-5} \text{ (photons at image point/photon from object point)}$$

While it is very difficult to compare resolution and efficiencies of different systems, nevertheless, and with this caveat, if a multi-channel collimator, having round holes in a hexagonal array has an efficiency G where G is given by:

$$G = [0.238 d^2 ad + t)]^2$$

where
d = hole diameter (typically 0.282 cm)
a = hole length (typically 2.54 cm)
t = septum thickness (typically 0.7 cm)
To approach a resolution of even 1 mm with a source to collimator distance of 2.5 cm, d must be $\leq 0.05$ cm. to yield $G \sim 4 \times 10^{-7}$. This collimator has been used for the higher energy $^{99m}$Tc 140 keV gamma rays, but even if $t = 0.05$ cm, $G = 1 \times 10^{-6}$, some twenty times lower than the crystal efficiency estimated above.

EXAMPLE III

Imaging $^{99m}$Tc 140 keV radiation

For the LiF (220) planes = $\theta_B = 1°49'$; $\lambda = 0.089$ Å $\sin\theta_B = 0.0316$; $\cos\theta_B = 0.995$.

For a distance from object to the end of the crystal pairs of 10 cm.

$$R = 15/2\sin\theta_B\cos\theta_B = 237.5 \text{ cm.}$$

So crystals should be bent to a radius of 475 cm and ground to a radius of 237.5 cm. Distance between faces of the crystals should be $$D = 4R\sin^2\theta_B = 0.95 \text{ cm.}$$

Many other crystals may be employed in the camera of the invention, particularly those with small d spacing, e.g., LiF(880) planes with $\theta_B = 37.6°$ for iodine x-rays. When using these higher order planes, it may be necessary to cool the crystals to reduce the thermal agitation effects (averaged deviations of atoms from their nominal positions because of thermal motion).

I claim:

1. An imaging device for focusing a two dimensional X-ray/gamma ray/neutron radiated object as a two dimensional image by Bragg diffraction comprising at least one single crystal bent to conform to the radius of a Rowland sphere of radius 2R and ground to fit snugly on a Rowland sphere of radius R and in motion relative to an axis normal to the axis of symmetry of the crystal.

2. A diffraction camera type imaging device as in claim 1 wherein the motion is rotary about said axis normal to the axis of symmetry.

3. A diffraction camera type imaging device as in claim 1 wherein the motion is translatory rectilinearly along said axis of symmetry.

4. A diffraction camera-type imaging device as defined in claim 1, including a pair of crystals each bent to conform to the radius of its Rowland sphere of radius 2R and ground to fit snugly on its Rowland sphere of radius R.

5. A diffraction camera-type imaging device including three pairs of crystals as defined in claim 1.

6. The invention defined in claim 5 wherein the crystal comprises LiF cleaved along its 220 planes.